United States Patent [19]
Clark

[11] Patent Number: 4,801,263
[45] Date of Patent: Jan. 31, 1989

[54] OSSEOUS IMPLANT SYRINGE

[76] Inventor: William C. Clark, P.O. Box 2777, Knoxville, Tenn. 37901

[21] Appl. No.: 87,597

[22] Filed: Aug. 19, 1987

Related U.S. Application Data

[63] Continuation-in-part of Ser. No. 867,065, May 27, 1986, abandoned.

[51] Int. Cl.⁴ .............................................. A61C 5/04
[52] U.S. Cl. ...................................... 433/90; 604/60; 604/218; 604/241
[58] Field of Search ............... 433/90, 89; 604/57–60, 604/218, 239, 241

[56] References Cited

U.S. PATENT DOCUMENTS

| | | | |
|---|---|---|---|
| 683,075 | 9/1901 | Schneider | 433/90 |
| 1,325,699 | 12/1919 | Oesterhaus | 604/59 |
| 1,469,004 | 9/1923 | Holtz | 433/90 |
| 2,505,028 | 4/1950 | Boeger . | |
| 2,754,590 | 7/1956 | Cohen . | |
| 3,424,158 | 1/1969 | Silver | 604/59 |
| 3,757,781 | 9/1973 | Smart | 604/59 |
| 4,060,083 | 11/1977 | Hanson | 604/59 |
| 4,551,135 | 11/1985 | Gorman et al. | 433/90 |
| 4,642,094 | 2/1987 | North et al. | 604/218 |

Primary Examiner—Carroll B. Dority, Jr.
Attorney, Agent, or Firm—Pitts and Brittian

[57] ABSTRACT

A device to place osseous implant substances into interdental alveolar bone defects. This device is an osseous implant syringe with an axial lumen of consistent cross-section to allow movement of the granular substance through the lumen. The granular substance is moved through the lumen by use of a syringe plunger member. Barrel caps are provided to prevent spillage of the osseous implant substance when the syringe is not in use. The outlet of the syringe is sufficiently small to effectively enter alveolar bone defects. An extension nozzle member is provided for those areas that cannot be reached by the syringe barrel member alone. An outlet cap can be placed over the extension nozzle member to prevent spillage when it is not in use. Furthermore, a plunger extension lengthens the syringe plunger member to completely dispense the osseous implant substance from the extension member. A curved extension nozzle member can also be attached to the end of the syringe barrel member to reach those areas that cannot be reached with a straight barrel. A filling device is provided for fast and efficient loading of the syringe barrel members.

16 Claims, 3 Drawing Sheets

OSSEOUS IMPLANT SYRINGE

This application is a continuation-in-part of U.S. patent application Ser. No. 867,065, filed May 27, 1986 and now abandoned.

TECHNICAL FIELD

This invention relates generally to a dental surgical device and is more specifically concerned with an osseous implant syringe capable of injecting osseous implant substances into interdental alveolar bone defects.

BACKGROUND

Osseous implant substances are used to fill interdental alveolar bone defects to effect bone grafts. These osseous graft materials are granular solids. The present technology for delivering osseous implant substances is to place the material in a sterile dappen dish and fill a delrin amalgam carrier from the dish. The osseous implant substance is then inserted into the graft site with the amalgam carrier. This process is slow, wasteful and difficult for the dentist and assistant as well. This technique requires many time consuming repetitions of the transfers on large or multiple grafts. The excessive time consumed in this method allows for slow hemorrhage of the graft site well before it is obturated, making firm condensation of the area more difficult and less effective. The surgeon's freedom to suction the defect area is curtailed on the transfer with an amalgam carrier because suction will remove any previously placed granular implant substances.

Various syringe devices have been devised for use in dentistry. One such device is shown in U.S. Pat. No. 2,754,590 issued to M. J. Cohen on Sept. 20, 1954. However, this device by Cohen would be ineffective to dispense the granular solid material that composes the osseous implant substance because of the inconsistent lumen dimensions; the granular material would pack at the change in lumen diameter and would not be expelled. Another such device is described in U.S. Pat. No. 2,505,028 issued to H. F. Boeger on Apr. 25, 1950. Again, this device cannot be used to dispense a granular material either because of the large reservoir going into the small dispensing outlet. There is no way at all to use this for a granular substance such as the osseous implant material. Furthermore, it would be difficult to use the invention shown by Boeger to reach the hard to reach areas of the gums because of the long distance from the tip of the needle to the body of the syringe. A final reference is made to U.S. Pat. No. 683,075 issued to A. Schneider on Sept. 24, 1901. The curved outlets from the syringe body would prevent the dispensing of any type of granular material. Furthermore, these outlets are too big to be used to insert into the small surgical incisions employed in dental surgery.

In any implant syringe it is necessary for the syringe to be the correct cross-sectional diameter to fit easily into graft sites through very small incisions. Smaller incisions are advantageous as they reduce the loss of implant substances after the procedure. The glass syringe presently used for edentulous augmentations is available in a variety of sizes, the smallest of which is 7 mm in diameter which is much too large to fit into most interdental osseous graft sites. It is also important for the implant syringe to contain a larger volume of implant substance than the capacity of an amalgam carrier to allow complete filling of osseous defects before the ever-present slow hemorrhage fills the defect. The implant syringe needs a curved nozzle to enable the surgeon an easier method to graft posterior and hard to reach areas. Preferably the syringe must have an outlet cap to prevent the spillage of implant materials and allow more than one barrel to be prepared at a time prior to the procedure which will reduce the procedure time ordinarily taken by reloading the amalgam carrier. Because no such satisfactory dental implant syringe exists serious problems arise due to the shortcomings of the prior art.

Accordingly, an object of the present invention is to provide an osseous implant syringe having a cross-sectional diameter that fits easily into graft sites through very small incisions. Smaller incisions are advantageous to reduce the amount of loss of the implant substances after the procedure.

It is another object of this invention to provide for a larger volume of implant substances than amalgam carriers which are now conventionally utilized. The greater volume allows complete filling of osseous defects before the ever-present slow hemorrhage fills the defect.

A further object of this invention is to provide a syringe for osseous implant applications that provides a curved delivery nozzle such that it is much easier for the surgeon to graft posterior and hard to reach areas.

It is also an object to provide a syringe constructed such that removable front and rear barrel caps allow one or more barrels to be prepared before the procedure starts which reduces the procedure time considerably and permits the possibility of grafting multiple osseous defects in a single procedure.

Still another object of this invention is to provide a syringe wherein the barrel is composed of delrin or a delrin-type material such that there is no chance of the device breaking while placed in an osseous defect and contaminating the graft site with glass fragments as is possible with glass syringes. Furthermore, since all components are made of delrin or flexible materials, the possibility of contaminating the implant substance with frictional debris from the syringe itself is reduced.

Still another object is to provide an osseous implant syringe that is autoclavable and thereby reusable, thereby permitting the surgeon to purchase synthetic osseous implant substances in bulk, load the barrels of the syringes according to the volume needed in each surgical procedure, and thus eliminate the waste inherent in fully pre-loaded syringes.

These and other features and advantages of the present invention will become apparent from a consideration of the following specification when taken in conjunction with the accompanying drawings.

SUMMARY OF THE INVENTION

The present invention provides an osseous implant syringe capable of injecting osseous implant substances into interdental alveolar defects. The syringe consists of a syringe plunger that is passed through an outer syringe barrel which contains the implant substances. As the syringe plunger is forced by hand through the syringe barrel, the displaced implant substances flow in a narrow stream from the outlet of the syringe barrel. When the syringe is not in use, a syringe barrel cap is placed on the outlet to keep the implant substances from flowing out of the outlet of the syringe barrel. A curved nozzle can be attached to the syringe barrel outlet to direct the implant substances to an area that is remote or impossible to access with a straight syringe barrel. The nozzle and the barrel have a consistent lumen diameter throughout the length of the syringe so as not to impede movement of the implant substances. The curved nozzle is attached to the syringe barrel by a thread-bearing nozzle coupler that is mounted on the outside of the syringe barrel. The syringe barrel cap also fits on the outlet of the curved nozzle to prevent the implant substance from flowing from the curved nozzle when the syringe is not in use. When the curved nozzle is used, a flexible plunger extension can be placed at the end of the syringe plunger such that it will conform with the curvature of the curved nozzle to fully displace the implant substances through the curved nozzle. The loading of the implant substances into the syringe barrel is accomplished by use of a filling device.

DETAILED DESCRIPTION OF THE EMBODIMENT

Figure 1:
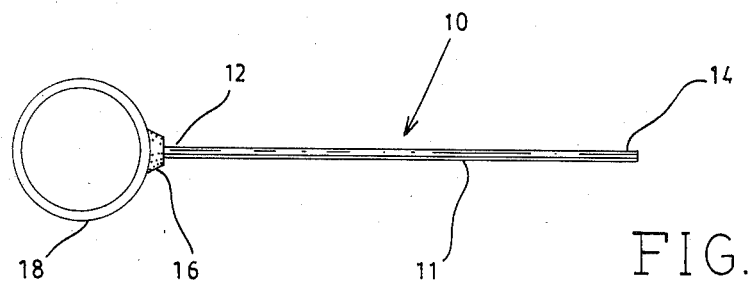
FIG. 1 is a side view of the syringe plunger member of the present invention.

Referring now to the drawings, and to the embodiment of the invention herein presented by way of illustration, FIG. 1 shows a syringe plunger member 10 as used in the invention. The syringe plunger member 10 consists of a piston rod 11 having a first end 12 and a second end 14. The syringe plunger member 10 also consists of a handle 18 connected to the first end 12 of the piston rod 11 as by a web support 16. In the preferred form, this syringe plunger member handle 18 is an open loop designed to accept a finger of the user.

Figure 2:
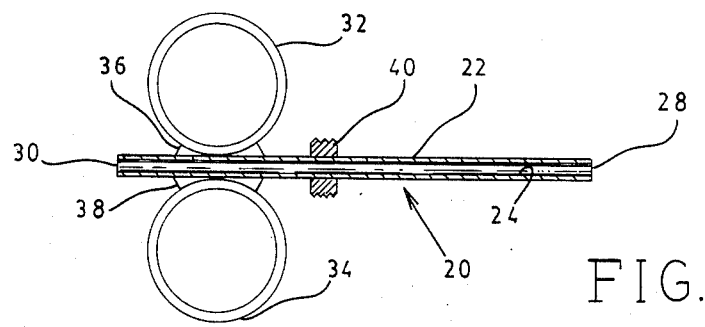
FIG. 2 is a longitudinal cross-sectional view of the syringe barrel member of the invention showing the lumen for closely receiving the syringe plunger member, and the threaded coupler for a nozzle.

Looking now to FIG. 2 of the drawings, it will be seen that the implant syringe includes a syringe barrel member 20. This syringe barrel member consists of a barrel sleeve 22 having an axial lumen 24 in which the piston rod 11 of the syringe plunger member 10 is slidably received. The difference in the outer diameter of the piston rod 11 and the inner diameter of the axial lumen 24 is large enough to allow the piston rod 11 to readily slide through the axial lumen 24 without allowing the implant substance to get between the piston rod 11 and the wall of the barrel sleeve axial lumen 24. As the piston rod 11 slides through the axial lumen 24, any implant substance therein is displaced and forced through the axial lumen 24 and out the syringe barrel outlet 28. It will also be seen that the syringe barrel member 20 consists of grasping members 32, 34 attached to the outer part of the barrel sleeve 22. The grasping members 32, 34 are typically attached to the barrel sleeve 22 by web supports 36, 38, respectively, attached to the outer surface of the barrel sleeve 22 and to the outside diameters of the grasping members 32, 34. Once again, these grasping members in their preferred form consist of two open loops to each accept one finger of the user. It is important to note that the diameter of the axial lumen 24 is consistent (unchanging) between a syringe barrel inlet 30 and the syringe barrel outlet 28.

Figure 3:
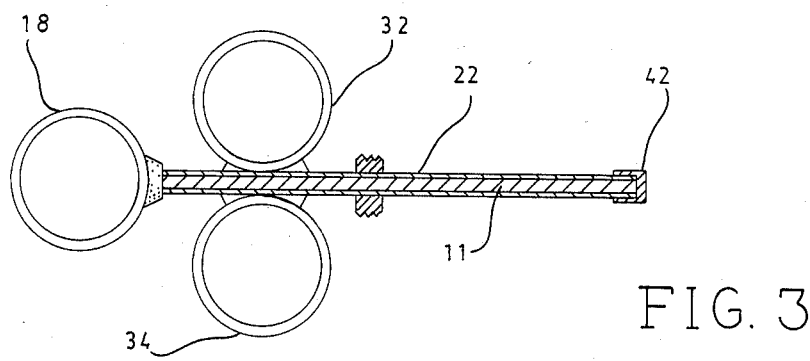
FIG. 3 is a longitudinal cross-sectional view of an assembled syringe with the syringe plunger member of FIG. 1 fitted within the syringe barrel of FIG. 2, and showing a syringe barrel cap at the outlet of the syringe barrel.

In FIG. 3 of the drawings it will be seen that the syringe plunger member 10 of FIG. 1 is placed slidably within the syringe barrel member 20 of FIG. 2. This is accomplished by placing the piston rod 11 in the syringe barrel inlet 30 of the axial lumen 24 and slipping the piston rod through the consistent diametered axial lumen 24. The piston rod 11, as it slides through the axial lumen 24, displaces any implant substance that is held within. This movement of the piston rod 11 is performed by exerting a force upon the syringe plunger member handle 18 toward the syringe barrel inlet 30 while exerting an equal and opposite force against the grasping members 32, 34. It will also be seen that a syringe barrel cap 42 can be placed over the syringe barrel outlet 28 when implant syringe is not in use to prevent implant substance spilling out of the syringe barrel outlet 28. A same type cap can be placed over the syringe barrel inlet 30 when the piston rod 11 is not placed within the axial lumen 24. Typically, as can be seen from this picture, the length of the piston rod 11 is the same as the length of the axial lumen 24 so as to accomplish complete displacement of implant substances from the lumen 24.

Figure 4:
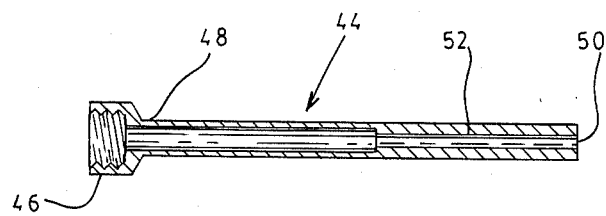
FIG. 4 is a longitudinal cross-sectional view of a straight extension nozzle member.

Referring now to FIG. 4, it can be seen that an extension nozzle member 44 can be provided for the implant syringe to reach those more distant areas of the mouth. The extension nozzle member 44 typically consists of an internally threaded extension member connector 46. This threaded extension member connector 46 releasably attaches to the threaded nozzle coupler 40 (see FIG. 2). The extension nozzle member 44 has a first end 48 and a second end 50. When this extension is attached to the syringe barrel member 20 the implant substance flows out of the syringe barrel outlet 28 and into the extension nozzle first end 48. It should be noted that the diameter of the axial lumen 24 of the barrel member 20 is the same as the diameter of an extension nozzle lumen 52.

Figure 5:
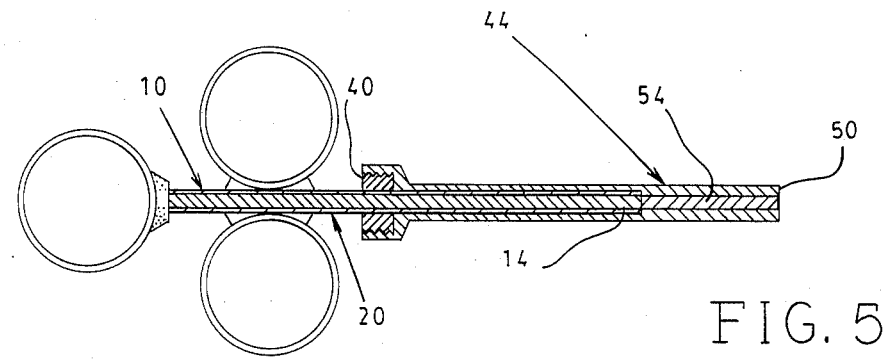
FIG. 5 is a longitudinal cross-sectional view of the assembled syringe with the extension nozzle member attached to the syringe barrel member.

Looking now at FIG. 5 of the drawings, it will be seen that the extension nozzle member 44 is placed on the syringe barrel member 20 by attaching the threaded nozzle coupler 40 to the threaded extension member connector 46. In order to assure displacement of the osseous implant substance all the way through the extension nozzle lumen 52, a plunger extension 54 is placed on the second end 14 of the syringe plunger member 10.

Figure 6:
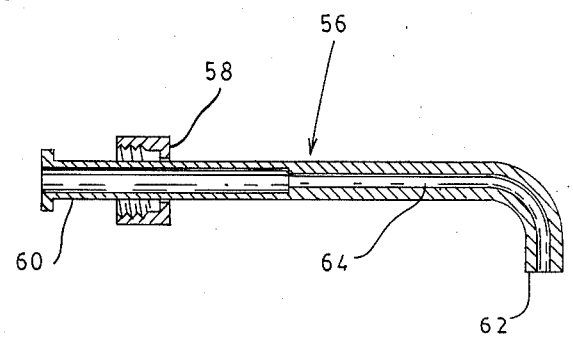
FIG. 6 is a longitudinal cross-sectional view of a curved nozzle member.

In FIG. 6 of the drawings it will be seen that a curved nozzle member 56 can be utilized with the barrel member 20. This curved nozzle member is provided with a threaded connector nut 58, a first end 60 and a second end 62, and a curved nozzle lumen 64. This curved nozzle lumen 64 has the same diameter as axial lumen 24 of the syringe member barrel 20.

Figure 7:
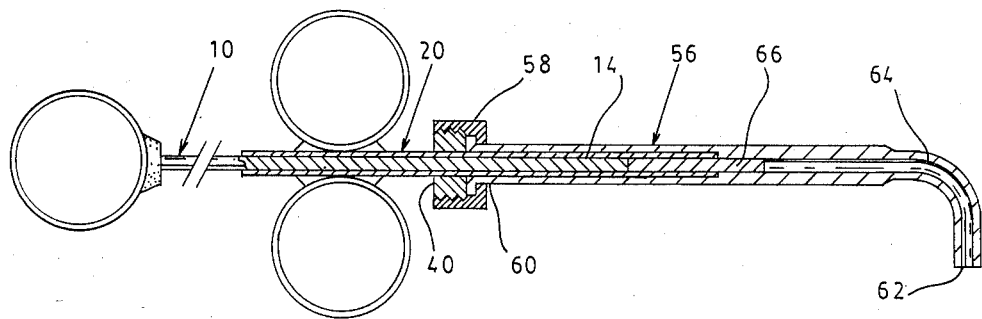
FIG. 7 is a longitudinal cross-sectional view of the implant syringe with the optional curved nozzle member connected to the nozzle coupler of the barrel member. Also shown in this drawing is a flexible plunger extension that is attached to the end of the syringe plunger member for the full displacement of the implant substances through the lumen of the curved nozzle member.

Referring now to FIG. 7 of the drawings, it will be seen that the curved nozzle member 56 of FIG. 6 can be attached over the syringe barrel member 20 to direct the flow of the implant graft substances to remote and hard-to-reach areas that are not reachable by the straight direction of the basic implant syringe or by the straight extension shown in FIGS. 4 and 5. The curved nozzle member 56 is attached to the threaded nozzle coupler 40 by the threaded coupler nut 58 which also allows the rotational angle of the curved nozzle member 56 to be adjusted. It can also be seen that when the curved nozzle member 56 is used, a flexible plunger extension 66 (similar to extension 54 of FIG. 5) can be placed on the second end 14 of the syringe plunger piston rod 11 so that the piston rod and its extension completely displace the implant substance through the curved nozzle lumen 64 of the curved nozzle member 56. Typically, the flexible plunger extentions 54, 66 can be fabricated of surgical quality rubber or the like. Likewise, the barrel caps 42 can be made of rubber or the like.

Figure 8:
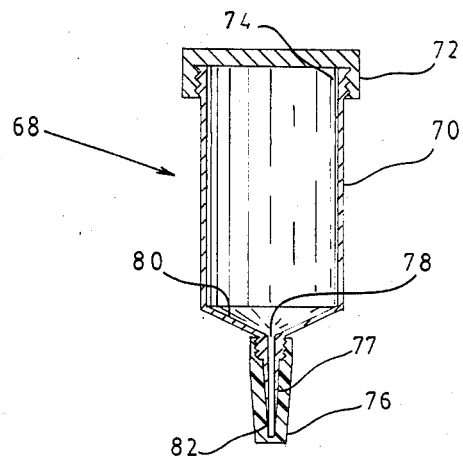
FIG. 8 is a cross-sectional view of a filling device for the syringe of the present invention with a cap on the inlet and a cap on the outlet to prevent spillage.

Referring now to FIG. 8 of the drawings, it will be seen that a filling device member 68 can be provided. This consists mainly of a filling device reservoir 70 which contains the implant substance until it is loaded into the syringe barrel member 20. The filling device is provided with an inlet cap 72 for the filling device inlet 74 which is removed for transferring gross quantities of implant substances into the filling device member 68. The filling device also has a cap 76 which is removed from the outlet neck 77 when the filling device is used to fill the syringe barrel member 20. The filling device reservoir 70 bottom has a sloping base 80 to allow the implant substance to more evenly flow into the outlet neck 77 and into the filling device outlet 78 for flow through a neck outlet 82. The substance is passed through the outlet neck 77 by a gentle shaking motion. The inlet cap 72 can be fastened to the filling device inlet by friction or by threads as shown. The cap 76 can be fastened to the outlet neck 77 by the same means.

Figure 9:
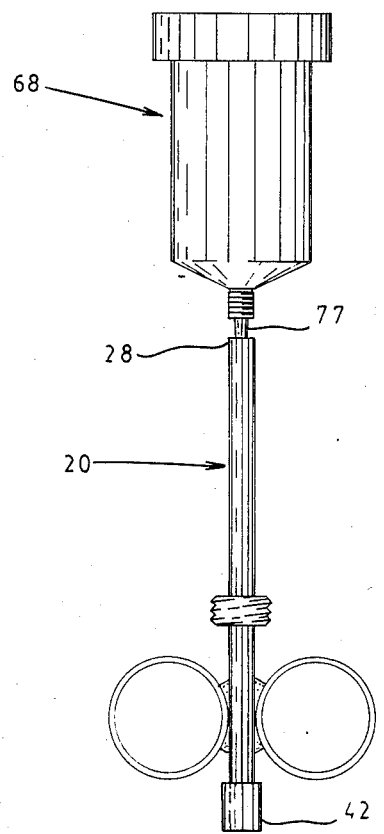
FIG. 9 is a side view of the filling device outlet attached to the syringe barrel outlet so as to load the implant substances from the filling device into the syringe barrel member.

Looking now at FIG. 9 it will be seen that the filling device member 68 is engaged with the syringe barrel member 20. The cap 76 (see FIG. 8) is taken off of the outlet neck 77 so that the filling device neck outlet 82 can be placed in the syringe barrel outlet 28. The granular substance is forced out of the filling device reservoir 70 down the outlet neck 77 and into the axial lumen 24 of the syringe barrel member 20 by a gentle shaking motion. This Figure also shows that the syringe barrel cap 42 can also be placed over the syringe barrel inlet 30 to prevent the granular material from flowing out of the inlet. The syringe barrel cap 42 allows for the syringe barrel member 20 to be filled and another syringe barrel cap 42 can be then placed over the syringe barrel outlet 28 after filling to prevent the escape of granular material from the syringe barrel outlet 28. This allows the syringe barrel member 20 to be set aside for quick and efficient usage when needed. With the exception of the flexible plunger extensions, each component is preferrably made of delrin or any sterilizable material capable of withstanding the forces necessary to apply the implant substance.

Although dimensions of the present invention are not critical, the following is an example of a typical syringe for osseous implant materials. The piston rod 11 of the syringe plunger member 10 has a 3 mm diameter and adapts closely to the axial lumen 24 of the syringe barrel member 20. The cross-sectional diameter of the outer part of the syringe barrel member 20 is approximately 4 mm to allow it to easily fit into a graft site through a very small incision. The length of the syringe barrel member 20 from the syringe barrel outlet 28 to the syringe barrel inlet 30 is approximately 4 inches. This length is a function of the required quantity of implant substance necessary for an implant and the distance over which the syringe is to traverse. The angle of the curved nozzle member 56 depends on the part of the mouth to be reached. As illustrated in FIGS. 6 and 7, it is typically 90 degrees, however other curvatures can be employed.

The use of the osseous implant syringe begins with the filling process. The inlet cap 72 of the filling device 68 is removed from the filling device inlet 74, and gross quantities of the osseous implant substances are transferred into the filling device inlet 74 by use of any suitable device. When the reservoir 68 is filled, the inlet cap 72 is replaced. The filling device member is then turned upside down and the cap 76 is removed from the outlet neck 77. With the barrel cap 42 removed, the syringe barrel member 20 is then placed such that the syringe barrel outlet 28 is upon the filling device neck outlet 82. A syringe barrel cap 42 is placed over the syringe barrel inlet 30. The units are then inverted such that the filling device member 68 is now resting on top of the syringe barrel member 20. The implant substance is then shaken through the outlet neck 77 and into the axial lumen 24 of the syringe barrel member 20. This process is continued until the osseous implant substance fills the axial lumen 24 of the syringe barrel member 20. The filling device member 68 is then removed and either the cap 76 is replaced or else another syringe barrel member 20 is filled using the same process. A syringe barrel cap 42 is then placed over the syringe barrel outlet 28.

When the syringe is to be used, the syringe barrel cap 42 is removed from the syringe barrel inlet 30 and the syringe plunger member 10 is placed in the axial lumen 24 through the syringe barrel inlet 30. The syringe barrel cap 42 on the syringe barrel outlet 28 is now removed and the syringe barrel outlet 28 is placed at the grafting site. If the syringe barrel member is too short to reach the graft site, the extension nozzle member 44 is placed onto the syringe barrel member 20 using the threaded nozzle coupler 40. A plunger extension 54 is placed at the second end 14 of the piston rod 11 of the syringe plunger member 10. A force is then applied to the syringe plunger member handle 18 by use of a thumb and an equal and opposite force is placed against the grasping members 32 and 34 by use of any two fingers such that the force pushes the granular substance through the axial lumen 24 and out the syringe barrel outlet 28. Once out of the syringe barrel outlet 28, the granular substance moves into the extension nozzle member 44, through the extension nozzle lumen 52, and out of the extension nozzle second end 50.

If however, a straight syringe barrel will not suffice, the curved nozzle member 56 can be attached to the syringe barrel member 20 by attaching the threaded nozzle member connection 58 to the threaded coupler 40. In this case, a flexible plunger extention 66 is placed against the second end 14 of the syringe plunger member 10. This allows displacement through the axial lumen 24 of the syringe barrel member 20 and also displacement through the curved nozzle lumen 64 and out the curved nozzle second end 62. The rotational angle of the curved nozzle member 56 is set by the amount of rotation of the threaded curved nozzle member connector 58 with respect to the threaded nozzle coupler 40. The syringe barrel cap 42 can be placed over the curved nozzle second end 62 of the curved nozzle member 56 or over the extension nozzle second end 50 of the extension nozzle member 44 to prevent spillage of the granular material when it is not in use.

It will be understood by those skilled in the art that the particular embodiment of the invention here presented is in no way restrictive; therefore, numerous changes and modifications may be made, and the full use of equivalents noted to, without departing from the spirit or scope of the invention as defined in the appended claims and their equivalents.

I claim:

1. An osseous implant syringe designed for injecting an osseous implant substance into interdental alveolar bone defects, comprising:
   a syringe plunger member having a piston rod and handle means connected at a first end of said piston rod;
   a syringe barrel member having a syringe barrel provided with an axial lumen from an inlet to an outlet to closely receive said piston rod of said syringe plunger member, said lumen having a uniform cross section throughout its length;
   grasping members attached to an external surface of said barrel sleeve proximate said barrel inlet; and
   a threaded nozzle coupler attached exterior to said barrel member proximate said grasping members.

2. The implant syringe of claim 1 further comprising a first syringe barrel cap for placement over said syringe barrel outlet to prevent spillage of said implant substance from said axial lumen.

3. The implant syringe of claim 2 further comprising a further syringe barrel cap for placement over said syringe barrel inlet when said piston rod of said syringe plunger member is not inserted into said axial lumen of said syringe barrel member, said first and further barrel caps to prevent spillage of said implant substance from said axial lumen.

4. The implant syringe of claim 1 further comprising an extension nozzle member having a first end and a second end and provided with an extension nozzle lumen, said first end of said extension member adapted for releasable attachment to said syringe barrel member by use of the said threaded nozzle coupler, said extension nozzle lumen having a consistent cross-section with said axial lumen of said barrel member.

5. The implant syringe of claim 1 further comprising a curved nozzle member having a first end and a second end and provided with a curved nozzle lumen, said first end of said curved nozzle member adapted for releasable attachment to said syringe barrel member by use of the said threaded nozzle coupler, said curved nozzle lumen having a consistent cross-section with said axial lumen of said barrel member.

6. The implant syringe of claim 4 further comprising a syringe barrel cap for placement over said extension nozzle member second end to prevent spillage of said implant substance.

7. The implant syringe of claim 5 further comprising a syringe barrel cap for placement over said curved nozzle member second end to prevent spillage of said implant substance.

8. An osseous implant syringe for injecting an osseous implant substance into interdental alveolar bone defects, which comprises:
   a barrel member having a syringe barrel inlet at a first end and a syringe barrel outlet at a further end, said barrel member provided with an axial lumen of a selected uniform cross section from said syringe barrel inlet to said syringe barrel outlet, said barrel member further provided with attached grasping members at said syringe barrel inlet;
   a syringe plunger member defined by a piston rod having first and second ends, said plunger member provided with handle means at said first end, said piston rod for being closely received in said lumen of said syringe barrel member;
   first coupler means attached to an external surface of said barrel member proximate said grasping members in a direction toward said further end of said barrel member; and
   a barrel extension member for releasable attachment to said syringe barrel member, said barrel extension nozzle member having a first end and a second end, said first end provided with further coupler means for releasable engagement with said first coupler means, said barrel extension nozzle member having an axial passage at said first end to accept said further end of said barrel member, and provided with a lumen from said first end to said second end of said barrel extension consistent in cross-section with said axial lumen of said syringe barrel member.

9. The syringe of claim 8 further provided with first and further barrel caps to releasably close said first end of said barrel member and said second end of said extension member, respectively, when said piston rod is withdrawn from said lumen of said barrel member.

10. The syringe of claim 8 further comprising a piston rod extension attached axially to said piston rod at said second end whereby said piston rod and piston rod extension extend from said first end of said barrel member to said second end of said barrel extension member.

11. The syringe of claim 8 wherein said barrel extension member is an axial extension for said barrel member, and wherein said lumen of said extension member is an axial extension of said lumen of said barrel member.

12. The syringe of claim 10 wherein said barrel extension member is curved from said first end thereof to said second end thereof, and thereby said lumen of said extension member is curved, and said piston rod extension is flexible to follow said curved lumen of said extension member as said piston rod is moved axially in said lumen of said barrel member.

13. The syringe of claim 8 wherein said first coupler means is an externally threaded collar attached to said barrel member, and said further coupler means is an internally threaded collar to cooperatively and releasably attach said barrel extension member to said barrel member.

14. The syringe member of claim 8 wherein said grasping members of said barrel means and said handle means of said plunger member are open loop-type members for accepting fingers of a user whereby said plunger member can be moved axially with respect to said barrel member.

15. An osseous implant syringe for injecting an osseous implant substance into interdental alveolar bone defects to effect bone grafts, which comprises:
 a substantially cylindrical barrel member having a first end and a further end, said barrel member provided with an axial lumen of a selected uniform cross-section from said first end to said further end, said barrel member further provided with loop-type grasping members at said first end to accept fingers of a user of said syringe;
 a plunger member defined by a piston rod having a first and further end, said piston rod provided with a loop-type handle at said first end to accept a finger of said user, said piston rod configured to be closely received in said lumen of said barrel member;
 an externally threaded coupler collar attached to an exterior surface of said barrel member proximate said grasping members in a direction toward said further end of said barrel member;
 a barrel extension member for releasable attachment to said barrel member, said extension member having a first end and a further end and being curved from said first end to said further and, said extension member provided with a curved lumen having a cross section consistent with said lumen of said barrel member;
 an internally threaded coupler collar carried by said first end of said extension member for releasable engagement with said coupler collar of said barrel member to effect said releasable attachment of said extension member and said barrel member; and
 a flexible piston rod extension attached to said further end of said piston rod whereby said piston rod extension traverses said curved lumen of said extension member as said piston rod traverses said lumen of said barrel member.

16. The syringe of claim 15 further comprising first and further barrel caps to releasably close said first end of said barrel member and said further end of said extension member when said piston rod is removed from said lumen of said barrel member.

* * * * *